United States Patent [19]

Jacovich et al.

[11] Patent Number: 5,395,728
[45] Date of Patent: Mar. 7, 1995

[54] HEXAHYDROXYBENZOPHENONE SULFONATE ESTERS OF DIAZONAPHTHOQUINONE SENSITIZERS AND POSITIVE PHOTORESISTS EMPLOYING SAME

[76] Inventors: Elaine C. Jacovich, 131 Fair Haven Dr., Middlebury, Conn. 06762; Wells C. Cunningham, 39 Maple Hollow Rd., New Hartford, Conn. 06057

[21] Appl. No.: 168,724

[22] Filed: Dec. 15, 1993

Related U.S. Application Data

[62] Division of Ser. No. 3,206, Jan. 12, 1993, Pat. No. 5,294,521, which is a division of Ser. No. 919,357, Jul. 23, 1992, Pat. No. 5,206,348.

[51] Int. Cl.$^6$ .......................... G03F 7/023; G03F 7/30
[52] U.S. Cl. ..................... 430/192; 430/165; 430/191; 430/193; 430/326; 534/557
[58] Field of Search ............. 430/192, 193, 165, 191, 430/326; 534/557

[56] References Cited

U.S. PATENT DOCUMENTS

| | | | |
|---|---|---|---|
| 3,637,384 | 1/1972 | Deutsch et al. | 430/192 |
| 4,863,828 | 9/1989 | Kawabe et al. | 430/192 |
| 4,871,645 | 10/1989 | Uenishi et al. | 430/192 |
| 5,128,230 | 7/1992 | Templeton et al. | 430/193 |
| 5,141,838 | 8/1992 | Aoshima et al. | 430/192 |
| 5,178,986 | 1/1992 | Zampini et al. | 430/192 |
| 5,206,348 | 4/1993 | Jacovich et al. | 534/557 |
| 5,294,521 | 3/1994 | Jacovich et al. | 430/192 |

Primary Examiner—Charles L. Bowers, Jr.
Assistant Examiner—John S. Chu

[57] ABSTRACT

Positive photoresists formulations for producing positive photoresist images having improved thermal stability yet which allow a wide variation in resin to photoactive sensitizer compound without significant changes in photospeed, thermal behavior, contrast or resolution and with virtually no less in unexposed areas of the photoresist and without significant outgassing or popping are provided by employing novel 1,2-diazonaphthoquinone-4- or -5- sulfonate esters of 2,3,4,3',4',5'-hexahydroxybenzophenone with a novel isomeric distribution of esters. The novel isomeric distribution of 1,2-diazonaphthoquinone-4- or -5- sulfonate esters of 2,3,4,3',4',5'-hexahydroxybenzophenone is characterized by two major isomers, together comprising at least about 70% by weight of the photoactive compound, and wherein the least polar isomer comprises only about 40%.

6 Claims, No Drawings

HEXAHYDROXYBENZOPHENONE SULFONATE ESTERS OF DIAZONAPHTHOQUINONE SENSITIZERS AND POSITIVE PHOTORESISTS EMPLOYING SAME

This is a divisional of application Ser. No. 8/003,206, filed Jan. 12, 1993, now U.S. Pat. No. 5,294,521, which is a divisional of Ser. No. 07/919,357, filed Jul. 23, 1992, now U.S. Pat. No. 5,206,348, issued Apr. 27, 1993.

FIELD OF THE INVENTION

This invention relates to formulations and processes for obtaining positive photoresist images. More particularly, this invention relates to novel photosensitizers for use in producing positive photoresists formulations permitting a wide variation in resin to photosensitizer ratio without a significant change in photospeed while producing positive photoresist images of improved thermal behavior and good contrast and resolution characteristics. Even more particularly this invention relates to novel photosensitizers that permit the production of positive photoresist images requiring lower photospeed and that can withstand high bake temperatures.

BACKGROUND OF THE INVENTION

It is well known in the art to produce positive photoresist formulations from alkali-soluble novolak resins together with light sensitive materials (photoactive compounds), usually a substituted naphthoquinone diazide compound which acts as dissolution rate inhibitor with respect to the resin, dissolved in an organic solvent or mixture of solvents. These photoresist formulations are applied as a thin film or coating to a substrate suitable for a particular application. Upon exposure of selected areas of the coated substrate to actinic radiation, the dissolution rate inhibitor or photoactive sensitizer causes the exposed areas of the coating to be more soluble in developer than the unexposed areas. Conversely, in those areas of the coated substrate not exposed to radiation, the photoactive compound inhibits dissolution of the photoresist film by the developer. Immersing the exposed substrate in alkaline developing solution causes the exposed areas of the photoresist coating to be dissolved while the unexposed areas are largely unaffected. Thus, a positive relief pattern is formed on the substrate. A similar process is used in lithographic printing plates as well.

Among the properties of a photoresist composition which are important in commercial practice and application are the following: photospeed of the resist, development contrast, resist resolution, thermal stability of the image, process latitude, line width control, clean development, unexposed film loss and the like.

Of greatly increasing importance is the ability of such photoresists to reproduce very small dimensions, for example sub-micron profiles or geometries, for use in electronic devices or components. Similarly important is the ability to produce such sub-micron profiles which can withstand high temperature environments or heat encountered in the device fabrication sequence. In processing steps which generate high heat, harsh plasma metal etching or ion implantation for example, the imaged resist must withstand the elevated temperatures with minimum or no critical dimension (CD) changes, edge rounding, and/or image or profile distortion or flow. Additionally, sidewall profiles must be as close to vertical as possible in order to obtain maximum replication of the masked critical dimension features during plasma etching or ion implantation. It is therefore desirable that the photoresist image be thermally stable at a temperature of 130° C. or above, preferably stable at a temperature of about 140°-150° C. or above, so that plasma etch and ion implantation steps among others can be made harsher and consequently allow faster processing.

It has been known for some time that positive photoresists based on high molecular weight novolak resins and diazonaphthoquinone compounds as sensitizers or photoactive compounds can produce reasonably stable images that can withstand temperatures as high as about 120°-125° C. without rounding or flowing or change of critical dimensions. However, as indicated hereinbefore, the geometries required have decreased dramatically and the fabrication process generates temperatures of 130° C. or higher. Photoresists able to provide photoresist images capable of withstanding such elevated temperatures cannot be easily accomplished solely by utilizing high molecular weight novolak resins. As the molecular weight of the novolaks go up, the resolution capabilities are generally reduced and resolution reduction is incompatible with the demands of high resolution devices wherein the geometries can be as low as 0.5 micron. Moreover, the fractionation of the novolak resins from suitable solvents necessary to obtain such high molecular weight novolaks, by eliminating or reducing the presence of low molecular weight novolak resin fractions, is cumbersome and results in undesirable yield loss and a slowing of photospeeds.

The photoactive compounds used today are generally sulfonate esters of diazonaphthoquinones and hydroxylic aromatics, such as those disclosed in U.S. Pat. Nos. 2,797,213; 3,106,465; 3,130,047; 3,148,983; 3,201,329; 3,785,825 and 3,802,885. It has also been recognized that the thermal resistance capabilities of positive photoresist images are improved as the diazo ester content of the photoresist formulation is increased. This is especially true for photoresist formulations containing esters of hydroxybenzophenones (HBP), e.g. tri- or tetra-hydroxybenzophenones, with diazonaphthoquinones (DNQ), e.g. 1,2-diazonaphthoquinone-4- or -5- sulfonyl chloride. However, as one increases the diazo ester content of the photoresist formulation, the solubility or shelf life of the formulation decreases. Yet, to be commercially viable, the formulation must survive at least one year without precipitation in the container.

Recently in U.S. Pat. No. 4,863,828 the use of 1,2-naphthoquinonediazide-4- or -5- sulfonate esters of 2,3,4,3',4',5'-hexahydroxybenzophenone as photoactive compounds for producing positive photoresist resins of improved thermal stability has been disclosed. However, while these esters of hexahydroxybenzophenone produce positive photoresist images having better thermal stability than those produced from corresponding esters of tri- or tetra-hydroxybenzophenones, the photospeed characteristics of the former are generally not as good as the latter. Furthermore, the esters of the hexahydroxybenzophenones do not permit a wide variation in ratio of novolak resin to photoactive compound without significant changes in photospeed, thermal behavior, contrast or resolution and without any significant loss in unexposed areas of photoresist.

It is therefore an object of this invention to provide novel photoactive compounds for use in providing positive photoresist formulations for producing positive photoresist images having improved thermal stability yet which allow a wide variation in resin to sensitizer ratio without significant changes in photospeed, thermal behavior, contrast or resolution and with virtually no loss in unexposed areas of the photoresist.

Another significant problem which results from high diazo ester content is the phenomenon called outgassing or popping which can occur when the coated photoresist is exposed to UV radiation by using exposure apparatus typically operating in a monochromatic mode, known as G-line, I-line, broad band and others. Typically, during exposure of such photoresist coatings, microscopic bubbles form in or next to the exposed areas. These bubbles result from the evolution of nitrogen, a material by-product of the UV induced reactions resulting from the diazo ester component. As the ratio of diazonaphthoquinone to the ketone in the tri-, tetra- or hexa-hydroxybenzophenone photoactive compound goes up, this phenomenon of outgassing or popping becomes more aggravated. This is particularly true when using esters of tetra- and hexa-hydroxybenzophenones with 1,2-diazonaphthoquinone-4- or -5- sulfonyl chloride, and especially when the ratio of DNQ/HBP is 3.5/1 or higher. Thus, one is confronted with the contradictory requirement of having a diazo-rich ester photoresist formulation to optimize thermal resistance, while trying, at the same time, to minimize or eliminate the phenomenon of outgassing or popping which becomes more severe as the diazo content in the photoresist increases.

It is therefore a further object of this invention to provide high temperature resistant photoresist images from high diazo ester containing positive photoresist compositions which do not suffer from the undesirable phenomenon of outgassing and/or popping during UV exposure.

A still further object of this invention is to provide means for obtaining positive photoresist images having improved thermal stability yet which allow a wide variation in the resin to sensitizer ratio without significant changes in photospeed, thermal behavior, contrast or resolution and with virtually no loss in unexposed areas of the photoresist while, at the same time, providing photoresist formulations wherein the undesirable phenomenon of outgassing or popping during UV exposure, even at high ratios of diazonaphthoquinone/ketone of hydroxybenzophenone, is avoided or substantially eliminated or greatly reduced.

SUMMARY OF THE INVENTION

It has been discovered that positive photoresists formulations for producing positive photoresist images having improved thermal stability yet which allow a wide variation in resin to photoactive sensitizer compound without significant changes in photospeed, thermal behavior, contrast or resolution and with virtually no loss in unexposed areas of the photoresist and without significant outgassing or popping are provided by employing novel 1,2-diazonaphthoquinone-4- or -5- sulfonate esters of 2,3,4,3',4',5'-hexahydroxybenzophenone. The novel photoactive compounds are produced by the reaction of diazonaphthoquinone-4- or -5- sulfonyl chlorides with 2,3,4,3',4',5'-hexahydroxybenzophenone in a manner to produce a novel isomeric distribution of esters that produce the hereinbefore described desired results when employed as the photoactive compound in positive photoresist formulations. The novel isomeric distribution of 1,2-diazonaphthoquinone-4- or -5-sulfonate esters of 2,3,4,3',4',5'-hexahydroxybenzophenone is confirmed by reverse phase HPLC analysis and is characterized by two major isomer peaks together comprising at least about 70%, preferably at least about 71%, by weight of the photoactive compound and wherein the least polar isomer comprises only about 40% generally about 37 to 44% and preferably about 39 to 42% by weight of the photoactive compound.

The isomeric distribution of 1,2-diazonaphthoquinone-4- or -5- sulfonate esters of 2,3,4,3',4',5'-hexahydroxybenzophenone is significantly different from the isomer distribution of 1,2-diazonaphthoquinone-4- or -5- sulfonate esters of 2,3,4,3',4',5'-hexahydroxybenzophenone produced according to the aforementioned U.S. Pat. No. 4,863,828. The isomeric distribution of the esters of said patent, as confirmed by reverse phase HPLC analysis, has a series of isomers having one major peak, the least polar isomer comprising greater than 81% by weight of the photoactive compound.

The invention comprises said novel esters, a process for production of said novel esters, positive photoresist resins formulations containing an alkali-soluble novolak resin and said novel esters in an organic photoresist solvent or mixture of photoresist solvents, substrates coated with said positive photoresist resin formulations and methods for forming photoresists or substrates employing said positive photoresist resin formulations.

DETAILS OF THE INVENTION

The photoresist formulations of this invention are formed by blending the necessary resin and photoactive compound ingredients in a suitable photoresist solvent. Such formulations comprise a base-soluble photoresist resin such as a novolak resin and like phenolic resins and the hereinbefore described photosensitizer compounds of this invention. Illustrative of phenolic resins employed in such systems are those novolak resins prepared by acid condensation of formaldehyde and phenol or an alkyl-substituted phenol under conditions described, for example, in Chemistry and Application of Phenolic Resins, Knop et al., Chapter 4, Springer Verlag, N.Y. 1979. Novolak resins derived from m-cresol alone or mixtures of m- and p-cresols and having average molecular weights in the range of about 600 to about 10,000 have been found to be particularly suitable for use.

The photoresist formulations contain the 1,2-diazonaphthoquinone-4- or -5- sulfonyl esters of 2,3,4,3',4',5'-hexahydroxybenzophenone having in reverse phase HPLC analysis, two major isomeric peaks which two isomers together comprise at least about 70% by weight of the photoactive compound and the least polar isomer comprises only about 40%, generally about 37 to 44%, by weight of said photoactive compound.

The photoresist formulations also generally comprise a solvent or mixture of solvents as well as optional components such as surfactants, colorants, anti-striation agents, dyes, leveling agents, speed enhancers, adhesion promoters, finely-divided pigments and the like. Illustrative of solvents employed alone or in admixture are ketones such as methylethyl ketone, methylisopropyl ketone, diethyl ketone and the like; chlorinated hydrocarbons such as trichloroethylene, 1,1,1-trichloroethane and the like; aliphatic alcohols such as ethanol, n-propyl alcohol, n-butyl alcohol, n-hexyl alcohol and the like; aliphatic esters such as n-butyl acetate, n-hexyl acetate, Cellosolve acetate, ethyl lactate, and the like; glycol ethers such as ethylene glycol monoethyl ether, propylene glycol monomethyl ether and esters thereof such as the acetates propionates and the like; and aromatic hydrocarbons such as toluene, xylene, anisole and the like, preferably ethyl lactate. The amount of solvent or mixture of solvents employed in the photoresist formulations is generally such as to represent from about 50 to about 90 percent by weight, and preferably from about 60 to about 80 percent by weight, based on total weight of the composition. The proportion of novolak resin in the formulations is generally of the order of about 2 to 45 percent and usually about 2 to 30 percent and preferably about 15 to 25 percent by weight. The proportion of novel photoactive sensitizer in the photoresist formulation is generally in the range of about 2 to about 20 percent and usually about 5 to 15 percent and preferably about 5 to 10 percent by weight.

When it is desired to utilize the photoresist formulation, a coating of the positive photoresist formulation is applied to a desired substrate such as aluminum, copper, copper-reinforced epoxy resin laminates, polymeric resins, quartz, silicon, silicon dioxide, silicon nitride, doped silica dioxide, tantalum and ceramic, wafers and the like. Any of the coating techniques known in the art can be employed in this step. Illustrative of such techniques are spin-coating, spraying, dipping, whirling, roller coating and the like. The surface of the substrate is generally cleaned by being pretreated chemically, depending upon the nature of the substrate material, using appropriate processes and compositions known in the art. The thickness of the coating applied to the substrate is generally of the order of about 0.5 to about 10 microns, but higher or lower thicknesses can be employed in any given instance.

The second step of the fabrication sequence comprises the soft-bake of the coating of photoresist on the substrate. The purpose of the soft-bake is principally to remove solvents present in the coating and also to promote adhesion of the photoresist to the substrate. The soft-bake step in the process of producing a photoresist image can be carried out conventionally at temperatures generally not exceeding about 110° C., and, in many cases, at temperatures as low as about 70° C., and for periods of time which can be as high as about 60 minutes. However, as disclosed in co-pending Application Ser. No. 07/524,678, the soft-bake step can, if desired, be carried out at a temperature in the range of about 120° C. to 160° C. for a period of time of at least 5 seconds, but not exceeding about 200 seconds and, preferably, not exceeding about 60 seconds. The most appropriate time to be used at any given temperature within the above range in the case of any given photoresist can be determined readily by a process of trial and error. This soft-bake step can be carried out using equipment and procedures conventional in the art. Illustratively, the step can be carried out by placing the resist-coated substrate in a convection oven, preheated to the desired temperature, for the chosen period to time. Alternatively, and preferably, the step is carried out on a conduction hot plate or like heating means as the resist-coated substrate is being process on in-line production equipment.

After the soft-bake step has been completed the coated substrate is subjected to imagewise exposure using actinic radiation (generally ultraviolet radiation) and employing procedures conventional in the art. The positive image is developed using appropriate developer solutions which, in the case of diazonaphthoquinone sensitizer systems, are aqueous alkaline solutions such as aqueous sodium or potassium hydroxide solution, sodium metasilicate, sodium orthophosphate, sodium hydrogen phosphate and the like. More aggressive developers comprise tetraalkylammonium hydroxides such as tetramethylammonium hydroxides in combination with surfactants and/or any of the above alkaline agents or as the sole or principal component of the developer.

The developed image, after washing with water to remove last traces of developer solution, is subjected to a post-bake also known as a hard-bake. Post-bake is employed to increase the resistance of the image to etching and other processes such as ion implantation and plasma etching to which the image and substrate may be subjected in subsequent steps in the formation of electronic component or device. The post-bake will generally be conducted at a temperature of from about 120°–160° C., preferably about 140°–150° C., for a period of from about 15 to about 90 seconds using equipment and procedures conventional in the art, i.e. in a convection oven or on a conduction hot plate.

The novel isomeric distribution of 1,2-diazonaphthoquinone-4- or -5- sulfonyl esters of 2,3,4,3′,4′,5′-hexahydroxybenzophenone are obtained by the esterification reaction of (1) diazonaphthoquinone-4- or -5- sulfonyl chloride or a mixture thereof with (2) 2,3,4,3′,4′,5′-hexahydroxybenzophenone in the presence of a suitable solvent such as N-methyl pyrrolidone and acetone and a catalytic amount of a catalyst mixture comprising a super nucleophilic esterification catalyst, e.g. 4-dimethylaminopyridine, and triethylamine. In the synthesis reaction of this invention a reaction product does not precipitate out until the reaction mixture is poured into a solution of dilute acid, e.g. dilute HCl.

A description of a general method for the preparation of the novel isomeric mixture follows. 2,3,4,3′,4′,5′-Hexahydroxybenzophenone (purified or unpurified) is dissolved in a mixture of acetone and N-methyl pyrrolidone, then 1,2-diazonaphthoquinone-4- or -5- sulfonyl chloride is added and also dissolved. Thereafter, a solution of 4-dimethylaminopyridine and triethylamine in acetone is added dropwise to the reaction mixture over a period of about 30 minutes with the temperature being controlled to a maximum of about 39° C. Following reaction of the mixture for about 1 hour, the mixture is quenched by the addition of a small amount of 10% HCl. The quenched reaction mixture is poured into dilute HCl and stirred, precipitating the reaction product. The product is filtered and washed with water and methanol, purified, and then dried in a vacuum oven.

In the above described esterification reaction a mixture of esters can be obtained wherein each of the compounds has different numbers of esterified hydroxy groups and different esterification positions. Thus, for example, if six moles of diazonaphthoquinone per mole of hexahydroxybenzophenone are employed all six of the hydroxyl groups of the hexahydroxybenzophenone could be esterified. If only 5.5 moles of diazonaphthoquinone per mole of hexahydroxybenzophenone are employed, an esterification ratio of about 92% results; if only 5 moles diazonaphthoquinone per mole of hexahydroxybenzophenone are employed, an esterification ratio of about 83% results; if only 4.5 moles of diazonaphthoquinone per mole of hexahydroxybenzophenone are employed, an esterification ratio of about 75% results; if only 4 moles of diazonaphthoquinone per mole of hexahydroxybenzophenone are employed, an esterification ratio of about 67% results. For purposes of illustrating the invention, in the following examples both the photoactive compounds of this invention and those prepared according to U.S. Pat. No. 4,863,828 are prepared, for comparison purposes, at the ratio level of 5.5 moles of 1,2-diazonaphthoquinone-4- or -5- sulfonyl chloride reactant per mole of the hexahydroxybenzophenone reactant.

The following specific examples provide detailed illustrations of the methods of preparing the novel isomeric photoactive esters of this invention, the photoresist formulations containing said photoactive compounds and the use of such photoresist formulations to produce photoresist images on substrates. The parts or percentages set forth in the examples are parts or percentages by weight unless specified otherwise. The novolak resins employed to produce photoresist formulations for testing were acid catalyzed formaldehyde/m-cresol/p-cresol condensates, either unfractionated having a molecular weight of about 7,000–8,000 or fractionated and having a molecular weight of about 9,000–10,000.

EXAMPLE 1

Hexahydroxybenzophenone was purified by heating a 10% solution in acetone for 15 minutes, allowing to cool and filtering through a Celite bed (a small amount of black material was seen on the Celite). Ten grams (0.04 m) of said purified 2,3,4,3',4',5'-hexahydroxybenzophenone was dissolved in a mixture of 200 ml N-methyl pyrrolidone and 100 ml of acetone in a round bottom flask. To this was added 53.16 gm (5.5 eq, 2.2 m) of 2,1,5-diazonaphthoquinone sulfonyl chloride and as soon as it was dissolved a solution of 27.5 ml triethylamine and 0.5 gm 4-dimethylaminopyridine in 15 ml of acetone was dropped in over 30 minutes. The temperature was monitored and its maximum was 39° C. The mixture was stirred for an additional 60 minutes and quenched by the addition of a small amount of 10% HCl. The reaction mixture was then poured into 1.5 l of dilute HCl and stirred overnight. The material was then filtered and washed with water until the filtrate was negative to silver nitrate. The wet cake was washed thoroughly with methanol and then dried to a constant weight in a vacuum oven. Yield 49.07 gm E398 nm=22,794 AU-1/cm-gm. Analysis for residual chloride showed 3437 ppm present. Karl Fischer titration showed 3.61% water present. HPLC analysis show approx. 1.4% residual benzophenone, no detectable sulfonyl chloride and the presence of two major isomer peaks for the product comprising at least about 70% by weight of the product, with the least polar of said two major isomers comprising about 40% by weight of the product.

EXAMPLE 2

Ten grams (0.04 m) unpurified 2,3,4,3',4',5'-hexahydroxybenzophenone was dissolved in a mixture of 200 ml N-methyl pyrrolidone and 100 ml acetone in a round bottom flask. To this was added 53.16 gm (5.5 eq, 2.2 m) of 2,1,5-diazonaphthoquinone sulfonyl chloride and as soon as it was dissolved a solution of 27.5 ml (19.97 gm) triethylamine and 0.5 gm 4-dimethylaminopyridine in 20 ml acetone was dropped in over about 30 minutes. The temperature was monitored and its maximum was 38° C. after about 35 minutes. The reaction was permitted to proceed for an additional 65 minutes with stirring and then quenched with the addition of about 20 ml 10% HCl. The reaction product was then poured into 2.5 l of dilute HCl (20 ml of 10% HCl added to water) and stirred overnight with the product precipitating out. The material was then filtered and washed with 6 l of deionized water. The product was then again filtered and thereafter the filtered product was placed in a vacuum oven until the water content was less than 2% by weight. Yield 46.73 gm E398 nm=23,226 AU-1/cm-gm. Analysis for residual chloride showed 4485 ppm present. Karl Fischer titration showed 1.91% water present. Reverse phase HPLC on analysis showed that the product produced two major isomer peaks comprising about 70.39% by weight, the least polar of these two isomers comprising about 39.39%.

EXAMPLE 3

The synthesis of Example 2 was repeated under identical conditions except that 10 gm of acetone purified 2,3,4,3',4',5'-hexahydroxybenzophenone was employed in place of the unpurified hexahydroxybenzophenone of Example 2. This example resulted in a yield of 46.21 gm of product. Reverse phase HPLC analysis showed that the product produced two major isomer peaks comprising about 72.14% by weight of the product, with the least polar of the two major isomers comprising about 41.40% by weight.

COMPARATIVE PRODUCT A

For purposes of comparison of the product of this invention with that of U.S. Pat. No. 4,863,828, an ester product of said patent was prepared according to the procedure described in said patent employing only a basic catalyst, i.e. triethylamine in acetone solvent. Ten grams (0.04 m) unpurified 2,3,4,3',4',5'-hexahydroxybenzophenone and 53.16 gm (5.5 eq, 2.2 m) 2,1,5-diazonaphthoquinone sulfonyl chloride were dissolved by stirring in 400 ml acetone in a round bottom flask. Then a mixed solution of triethylamine/acetone (19.97 gm/50 ml) was gradually added dropwise over a period of about 47 minutes, an orange precipitating starting to form after about 34 minutes, the reaction temperature reaching a maximum of about 34° C. The reaction was conducted over a period of four hours. The reaction was not quenched. After four hours the reaction product was added dropwise to 2.5 l of 1% aqueous HCl. The product mixture was stirred overnight, washed with 6 l water, filtered and the product placed in a vacuum oven until the water content was less than 2%. Yield 53.03 gm. Reverse phase HPLC analysis in the manner identical to Examples 1, 2 and 3 showed that the esterified product of this comparative product displayed only one major isomer peak, said peak comprising about 81.28% by weight.

COMPARATIVE PRODUCT B

A 2,1,5-diazonaphthoquinone sulfonyl chloride esterification product of 2,3,4,3',4',5'-hexahydroxybenzophenone is marketed by Toya Gosei Chemical Co. and is believed to be produced according to the method described in U.S. Pat. No. 4,863,828. Some of said Toya Gosei product was acquired from them and analyzed by reverse phase HPLC which showed that the product displayed only one major isomer peak, said peak comprising about 73.98% by weight of the product.

EXAMPLES 4 to 9

Positive photoresist compositions were prepared by admixture of the following components:

| Component | Parts |
|---|---|
| Novolak resin* | 18.98 |
| sensitizer** | 6.33 |
| Ethyl lactate | 14.68 |
| Surfactant | 0.05 |

*acid catalyzed formaldehyde/m-cresol/p-cresol condensate, either-unfractionated having a molecular weight of about 7,000 to 8,000 or fractionated having a molecular weight of about 9,000 to 10,000.
**esterified 1,2-naphthoquinonediazide-5-sulfonate of 2,3,4,3',4',5'-hexahydroxybenzophenone.

The sensitizer is present in an amount to provide a resin/sensitizer ratio of 3:1. Ultraviolet absorption at 398λ was determined to ascertain the diazo content.

Photoresist composition was spin coated on HMDS primed silicon wafers employing a SVG 8126 photoresist coater and baked on a conductive hot plate for about 50 seconds at a temperature of about 110° C. Spin speeds were varied so that all films produced were 1.1 microns thick. The photoresist was imagewise exposed through a mask on a Perkin-Elmer Microlign 130. Development was with two 20 seconds puddles of Tokyo Ohka NMD-3 (tetramethylammonium hydroxide based) developer.

EO values were derived from exposure on the Perkin-Elmer Microlign 130 through an Optiline Step Tablet that allows calculation of the energy needed to clear the film. The developed wafer was cut into forty-nine (49) die and each was observed for microscopic bubbles and evidence of the occurrence of outgassing and/or popping.

Thermal studies were performed on patterned wafers which were subjected to a 5 minutes hot plate bake at 130° C. SEM photographs were taken to determine if there had been any rounding or deformation of large, >5 micron, features.

Results of said testing of the photoresists are set forth in the following table wherein the photospeed advantage for the photoresist compositions employing the sensitizer of the invention compared to the prior art sensitizer is clearly demonstrated. Similarly, the results show that the sensitizers of this invention eliminate or substantially eliminate the popping or out-gassing phenomena that occurs with photoresists employing the prior art esters of hexahydroxybenzophenones.

EXAMPLE 10

The photosensitizer of Example 1 was employed with unfractionated acid catalyzed formaldehyde/m-cresol/p-cresol condensate novolak resin having a molecular weight of about 7,000 to 8,000 and ethyl lactate solvent and surfactant to provide photoresist compositions. However, various ratios of novolak resin/sensitizer were employed in the photoresist compositions. The various photoresist compositions were then coated in film thicknesses of between 1.37 and 1.39 microns on substrate, exposed and developed in the same manner as described for Examples 4 to 9. Photospeed for the various photoresist composition with the different resin/sensitizer ratios was similarly determined. Results were as follows:

| Resin/Sensitizer Ratio | EO (mj/cm$^2$) |
|---|---|
| 3:1 | 102 |
| 3.5:1 | 104 |
| 4:1 | 107 |
| 5:1 | 133 |
| 6:1 | 175 |

The test results indicate the wide formulation latitude possible, with the ester sensitizers of this invention, without any significant variance in photospeed. In fact, almost no difference in photospeed occurs between resin/sensitizer ratios of from 3:1 to 4:1.

The lower and essentially unchanged photospeed property obtained with photoresist compositions containing the ester sensitizers of the invention in various resin/sensitizer ratio permits the option of contrast improvement through process and/or developer choice, options not available with the esters produced according to U.S. Pat. No. 4,863,828 or the esters available from Toya Gosei.

Tests were conducted to demonstrate that the speed effects of the novel esters of this invention are not due to residual reactants. Three photoresist formulations were prepared using novolak resin, the Toya Gosei esters, ethyl lactate solvent and surfactant. In one formulation the Toya Gosei esters employed were spiked with 8% 2,3,4,3',4',5'-hexahydroxybenzophenone and in a second formulation the Toya Gosei ester was spiked with 3200 ppm 2,1,5-diazonaphthoquinone sulfonyl chloride. The third formulation was a control formulation employing a non-spiked Toya gosei ester sensitizer. No significant difference in photospeed between

| Example No. | Novolak* | Sensitizer | EO (mj/cm$^2$) | Number of 49 dice displaying "popping" | Total Number of "pops" per wafer | Post Bake 5μ line 130° C. 5 minutes |
|---|---|---|---|---|---|---|
| 4 | U | Example 3 | 37.3 | 0 | 0 | Slight rounding |
| 5 | F | Example 3 | 52.3 | 2 | 3 | Slight rounding |
| 6 | U | Comparative Comp. A | 103.1 | 9 | 14 | Slight edge pull back, no rounding |
| 7 | F | Comparative Comp. A | 134.7 | 9 | 13 | Slight edge pull back, no rounding |
| 8 | U | Comparative Comp. B | 126.6 | 24 | 38 | Slight edge pull back, no rounding |
| 9 | F | Comparative Comp. B | 148.2 | 49 | >4600 | Slight edge pull back, no rounding |

*U = unfractionated
*F = fractionated the control formulation and those employing the spiked esters was observed to account for the photospeed difference between photoresist compositions employing the esters of this invention (Examples 4 and 5) and the photospeed of the photoresist compositions containing the Toya Gosei ester sensitizer (Examples 8 and 9).

The novel photosensitizer ester products of this invention provide photoresist compositions which produce better thermal properties in resist patterns produced therefrom than the thermal properties obtained for resist patterns produced from 1,2-diazonaphthoquine-4- or -5- sulfonate esters of tri-, tetra- or pentahydroxybenzophenones. In addition, the novel photosensitizer ester products of this invention provide photoresist compositions that permit wide formulation latitude, especially in resin/sensitizer ratio, with wide variance in photospeed requirements whereas corresponding photoresist compositions containing as the photosensitizer, 1,2-diazonaphthoquinone-4- or -5- sulfonate esters of tri-, tetra-, penta- or even the hexa-hydroxybenzophenones of U.S. Pat. No. 4,863,828 or available from Toya Gosei cannot produce such results.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A positive photoresist composition comprising in admixture:
    (a) a bindingly effective amount of an alkali soluble novolak resin and
    (b) a light sensitive effective amount of a photosensitizer, said photosensitizer comprising an isomeric mixture of a 1,2-diazonaphthoquinone-4- or -5- sulfonate ester product of 2,3,4,3',4',5'-hexahydroxybenzophenone said ester product producing, by reverse phase HPLC analysis, two major isomer peaks, said two major isomers comprising at least about 70% by weight of the ester product and wherein the least polar isomer of said two major isomers comprises only about 37 to 44% by weight of the product.

2. A positive photoresist composition comprising:
    (a) a bindingly effective amount of an alkali soluble novolak resin and
    (b) a light sensitive effective amount of a photosensitizer, said photosensitizer comprising a 1,2-diazonaphthoquinone-4- or -5- sulfonate ester product of 2,3,4,3',4',5'-hexahydroxybenzophenone according to claim 1 wherein the ester product is a 1,2-diazonaphthoquinone-5-sulfonate ester and the least polar isomer of the two major isomers comprises about 39 to 42% by weight.

3. A positive photoresist composition comprising:
    (a) a bindingly effective amount of an alkali soluble novolak resin and
    (b) a light sensitive effective amount of a photosensitizer, said photosensitizer comprising a 1,2-diazonaphthoquinone-4- or -5- sulfonate ester product of 2,3,4,3',4',5'-hexahydroxybenzophenone according to claim 1 wherein said product is produced by reacting 1,2-diazonaphthoquinone-4- or -5- sulfonyl chloride or a mixture thereof with 2,3,4,3',4',5'-hexahydroxybenzophenone in the presence of a solvent and a catalytic amount of a super nucleophilic esterification catalyst and triethylamine at a temperature of no greater than about 39° C. and thereafter adding said reaction mixture to a solution of a dilute acid to precipitate out the desired product.

4. A positive photoresist composition comprising:
    (a) a bindingly effective amount of an alkali soluble novolak resin and
    (b) a light sensitive effective amount of a photosensitizer, said photosensitizer comprising a 1,2-diazonaphthoquinone-4- or -5- sulfonate ester product of 2,3,4,3',4',5'-hexahydroxybenzophenone according to claim 3 produced by reacting about 5.5 molar equivalents of 1,2-diazonaphthoquinone-5-sulfonyl chloride with one molar equivalent of 2,3,4,3',4',5'-hexahydroxybenzophenone in the presence of N-methylpyrrolidone and acetone solvents and a catalytic amount of 4-dimethylaminopyridine and trimethylamine catalysts and precipitating the desired product by adding the reaction mixture to a solution of dilute HCL, said product producing, by reverse phase HPLC analysis, two major isomer peaks comprising at least about 71% by weight of the product and the least polar of said two major isomers comprising about 39 to 42% by weight.

5. A positive photoresist composition according to claim 1 wherein the weight ratio of novolak resin to photosensitizer is from about 3:1 to 4:1.

6. A positive photoresist composition according to claim 2 wherein the weight ratio of novolak resin to photosensitizer is from about 3:1 to 4:1.

* * * * *